United States Patent [19]
Busch

[11] Patent Number: 5,156,167
[45] Date of Patent: Oct. 20, 1992

[54] ACCESSORY DRAPE FOR USE BY AN ANESTHESIA PROVIDER

[76] Inventor: Lyndon J. Busch, 3921 Overton Park East, Fort Worth, Tex. 76109

[21] Appl. No.: 626,620

[22] Filed: Dec. 7, 1990

[51] Int. Cl.⁵ ............................................. A61B 19/10
[52] U.S. Cl. .................................... 128/852; 128/849
[58] Field of Search ............... 128/846, 849, 852, 855, 128/850, 851, 853, 854

[56] References Cited

U.S. PATENT DOCUMENTS

| | | | |
|---|---|---|---|
| Re. 27,710 | 7/1973 | Melges | 128/852 |
| 3,763,857 | 10/1973 | Schrading . | |
| 3,856,005 | 12/1974 | Sislian | 128/849 |
| 3,955,569 | 5/1976 | Krzewinski et al. | 128/855 |
| 4,027,665 | 6/1977 | Scrivens . | |
| 4,553,538 | 11/1985 | Rafelson | 128/852 |
| 4,720,881 | 1/1988 | Meyers . | |
| 4,976,274 | 11/1990 | Hanssen | 128/849 |

Primary Examiner—Robert A. Hafer
Assistant Examiner—Sam Rimell
Attorney, Agent, or Firm—Townsend and Townsend

[57] ABSTRACT

A suction drape is shown for use by an anesthesia provider during a surgical procedure to temporarily hold a suction instrument. The drape is adapted to be received on a hospital operating room table and includes a main sheet of flexible, drapable material including a head region received beneath a patient's head having a pocket fold which defines an accessory receiving pocket. An envelope region is formed beneath the head region by folding a portion of the main sheet back upon itself. The envelope region defines a second accessory receiving pocket for the drape and further anchors the drape to the table during use.

6 Claims, 4 Drawing Sheets

ACCESSORY DRAPE FOR USE BY AN ANESTHESIA PROVIDER

BACKGROUND OF THE INVENTION

1. Field of the Invention

The present invention relates generally to drapes of the type used in caring for a medical patient, such as during surgical procedures and, more specifically, to a suction drape used by an anesthesia provider during surgical procedures to temporarily hold a suction instrument and to limit its contamination.

2. Description of the Prior Art

The practice of anesthesia today is a highly technical science involving various instruments and instrumentation. As a result, the work environment of the anesthesia provider is congested by numerous items necessary for the performance of various surgical procedures. During any given surgical procedure, the anesthesia provider is surrounded by numerous electrical monitoring devices, machines that mix anesthetic gases, ventilate a patients lungs, evacuate fluids, administer and warm fluids and warm the patient's body. Although the anesthesia provider is surrounded by an elaborate array of medications, syringes, needles, and tubings of various descriptions, a temporary, clean or sterile receptacle is not always available for such accessories. Because of the lack of a standardized receptacle or holder, such items are not always within easy reach.

Especially today, limiting patient contamination of the work environment, personnel and of subsequent patients is of primary importance. In suctioning saliva, blood, nasal secretions and gastric secretions, there is the potential for contamination with these fluids and infectious agents which they may contain such as, for example, hepatitis and the AIDS virus.

U.S. Pat. No. 4,720,881, issued Jan. 26, 1988, to Meyers, shows an anesthesia accessory unit which comprises a rigid tray assembly adapted to be supported on an end portion of a patient's bed structure, normally a hospital operating room table. While this device offers a number of convenient receptacles, it is non-disposable in nature and relatively expensive to manufacture. Also, the receptacle areas are not provided in the form of clean or sterile pockets which could be closed about the contaminated portion of a surgical instrument to prevent contamination of surrounding work areas, personnel, or subsequent patients.

The provision of a disposable drape, particularly adapted for receiving anesthesia accessories, would provide a disposable article which could be inexpensively produced and which would not need to be laundered or re-sterilized since it would be intended for only a single use. While disposable drapes have increased in use in hospitals in recent years none, to Applicant's knowledge, have been tailored specifically for use as an accessory holder for anesthesia instruments for use during surgical procedures to limit contamination from these devices.

The present invention has as an object to provide an accessory holder for a medical care provider, such as an anesthesia provider, in the form of a disposable drape adapted to be received on an end of a patient support structure, such as a hospital operating room table.

Another object of the invention is to provide such a drape having accessory receiving pockets which define clean or sterile enclosures for temporarily holding a variety of accessories and instruments during surgical procedures.

Another object of the invention is to provide a disposable drape having pockets for receiving a suction instrument during anesthesia operations which provides a sterile environment for the instrument and avoids contamination of the surrounding work area, personnel, or subsequent patients.

Another object of the invention is to provide an accessory drape for use during anesthesia operations which eliminates the need for a second person standing by the anesthesia provider to lend assistance when certain items are needed.

Another object of the invention is to provide an accessory drape which improves the dexterity of the anesthesia provider by freeing a hand or hands during surgical procedures by providing a convenient clean or sterile receptacle for the anesthesia accessories being utilized.

Another object of the invention is to provide an accessory drape installable upon a variety of hospital operating room tables, stretchers and patient supports of various manufacturer's designs, so that the accessory drape can be standardized from one operating room to another.

SUMMARY OF THE INVENTION

The accessory drape of the invention is intended for use by an a medical care provider, such as an anesthesia provider, during surgical procedures. The drape is adapted to be received on a patient support structure of the type having a head support at one end for a patient's head. The drape includes a main sheet of flexible, drapable material, the main sheet having a head region adapted to be received beneath a patient's head when the patient's head is received on the head support for anchoring the drape to the patient support structure. The head region includes a pocket fold which defines a first accessory receiving pocket for the drape. An envelope region is formed beneath the head region of the drapable material. The envelope region defines a second accessory receiving pocket for the drape. The envelope region is adapted to be received beneath the patient head support to thereby further anchor the drape to the patient support structure.

The first accessory receiving pocket has a top layer and a bottom layer, each of which has a front edge, a rear edge and opposing side edges. The front edge of the top layer is recessed to facilitate the insertion of accessories within the pocket during surgical procedures. Preferably, the drape includes at least one additional accessory receiving pocket formed by a pocket fold in the main sheet of the flexible, drapable material, the additional accessory receiving pocket being arranged to depend downwardly from the head region of the drape generally perpendicular to the plane thereof when the drape is received on the patient support structure.

The accessory drape of the invention is particularly suited for use as a suction drape to temporarily hold a suction instrument during surgical procedures where the suction drape is received on a hospital operating room table of the type having a cushioned head support for a patient's head at one end thereof.

Additional objects, features and advantages will be apparent in the written description which follows.

BRIEF DESCRIPTION OF THE DRAWINGS

in FIG. 1 showing the first accessory receiving pocket, envelope region and one additional accessory receiving pocket with the folds being exaggerated for ease of illustration;

in FIG. 5;

in FIG. 7;

in FIG. 9.

DETAILED DESCRIPTION OF THE INVENTION

Figure 1:
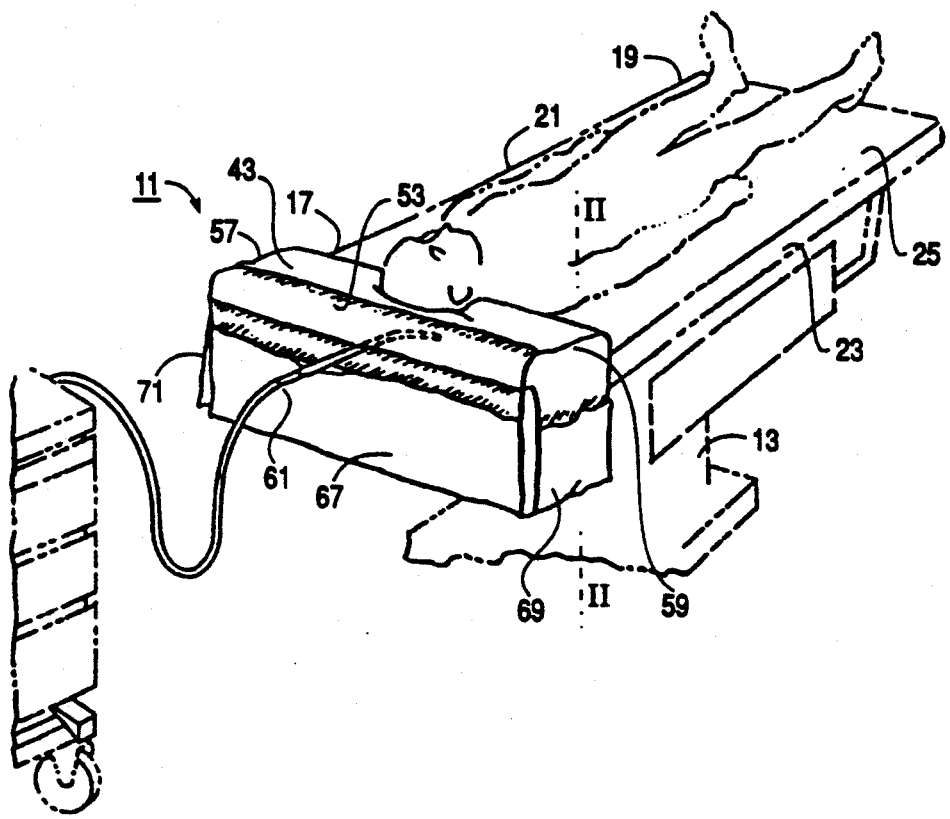
FIG. 1 is a simplified, perspective view of a patient support structure, in this case a hospital operating room table, showing the accessory drape of the invention installed at the head of the table, the drape being used to receive a suction instrument of the type used during a surgical procedure.

FIG. 1 shows an accessory drape of the invention designated generally as 11 which is intended for use by a medical care provider, such as an anesthesia provider (Anesthesiologist or Anesthetist), during surgical procedures in an operating room, emergency room or in any other area where accessories such as a suction instrument are used. The accessory drape has as its primary purpose to reduce contamination of the surrounding area and/or personnel due to body fluids which occur in routine use of a suction apparatus to suction the oral cavity, nasal passages and in some cases suction of the stomach.

The accessory drape 11 is adapted to be received on a patient support, typically a hospital operating room table, such as table 13 shown in FIG. 1. As will be apparent, the accessory drape 11 can also be utilized on other patient supports, such as a stretcher found in an emergency room, recovery room or intensive care unit. A number of operating room tables, such as the table shown in FIG. 1, are available commercially with either moveable or fixed bases. The fixed-base table is typically available with interchangeable table tops to meet the needs of specific surgical specialties and will be familiar to those skilled in the art. The standard operating room table has three or more hinged sections including a head support (shown in isolated fashion as 15 in FIG. 2) that can be pivoted or flexed at hinged locations. Special operating tables are available, e.g., genitourinary, orthopedic and ophthalmologic surgery.

As seen in FIG. 1, the patient support structure 13 will include a head 17, a foot 19 and opposing sides 21, 23 which define a horizontal plane of rest for a patient (shown in dotted lines in FIG. 1). The head support 15 located at the head 17 of the table can be, for example a cushion which elevates the patient's head slightly above the horizontal plane 25, the cushion being pivotable about an axis which approximately transverses the patient's neck region.

Figure 3:
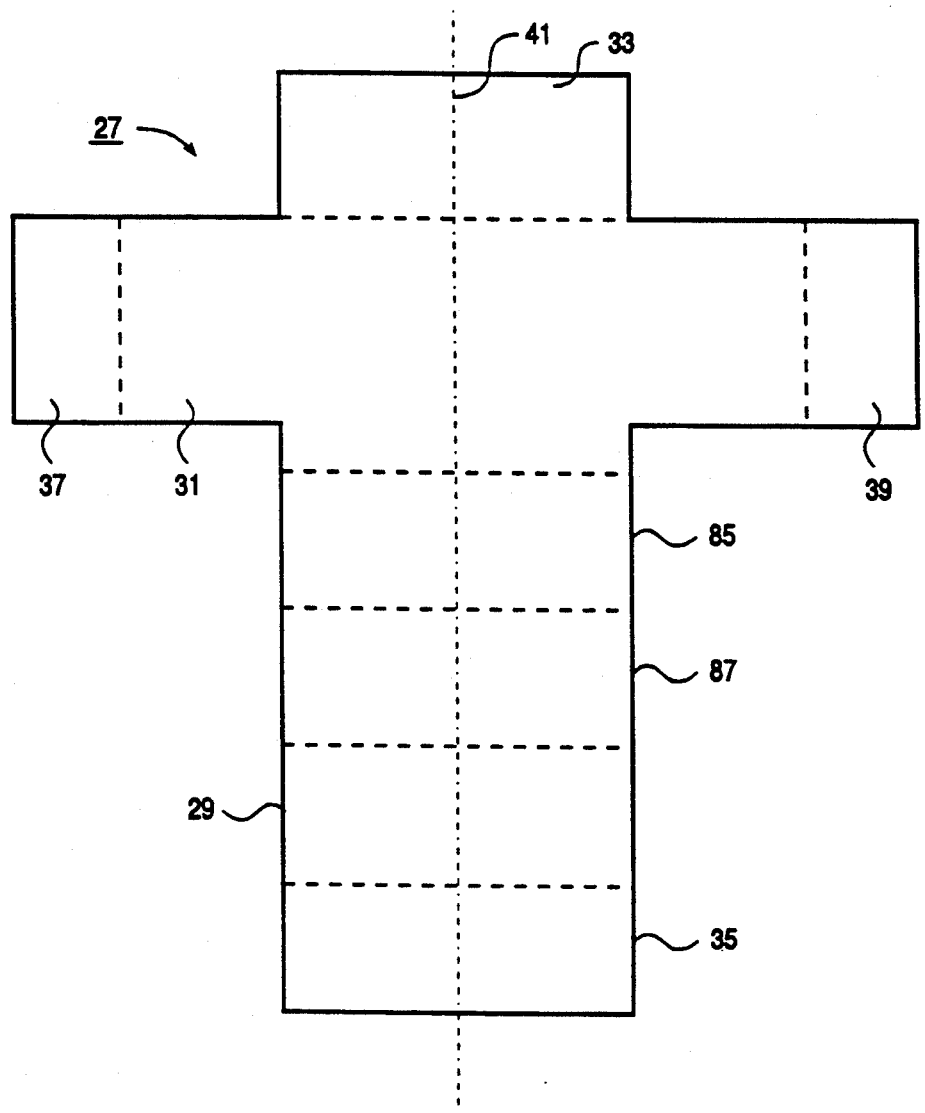
FIG. 3 is a plan view of the main sheet of flexible, drapable material used to form the accessory drape of the invention.
Figure 11:
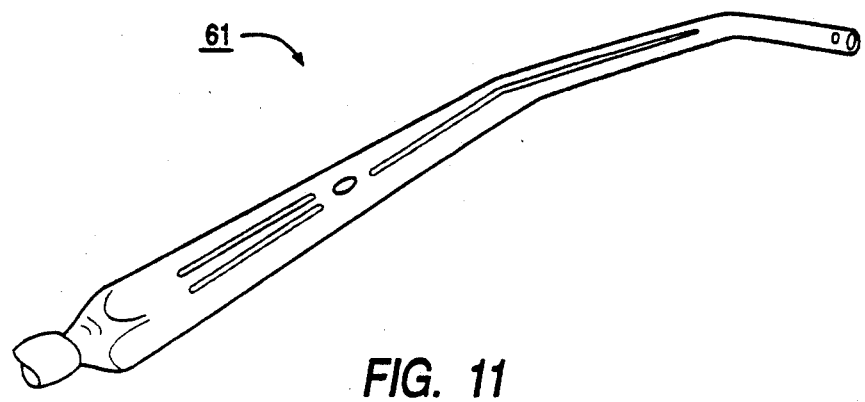
FIG. 11 shows a surgical suction instrument.
Figure 4:
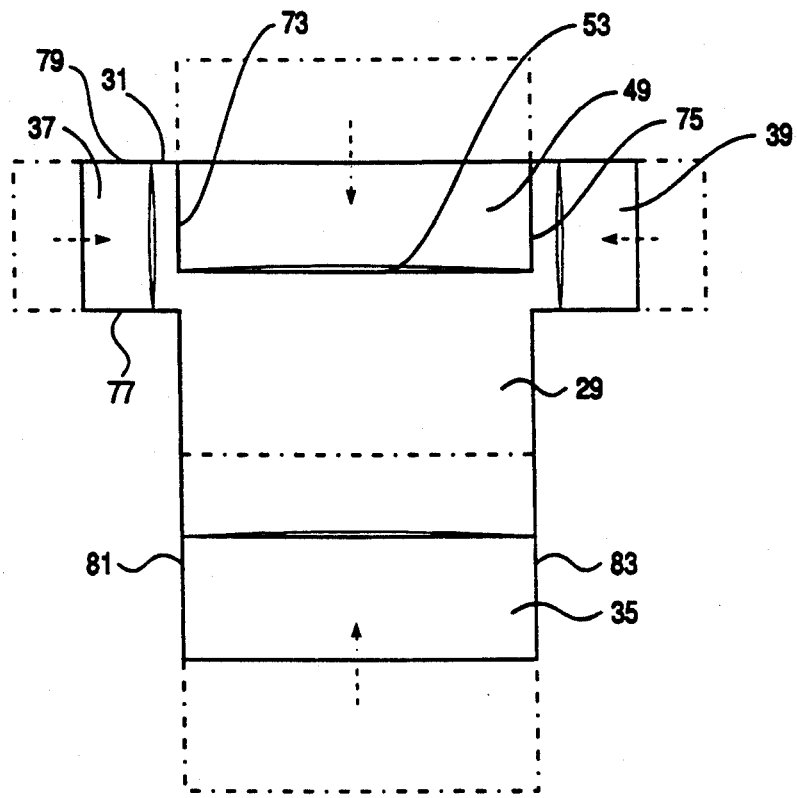
FIG. 4 is a view similar to FIG. 3 showing the initial folds used to form the accessory receiving pockets.
Figure 5:
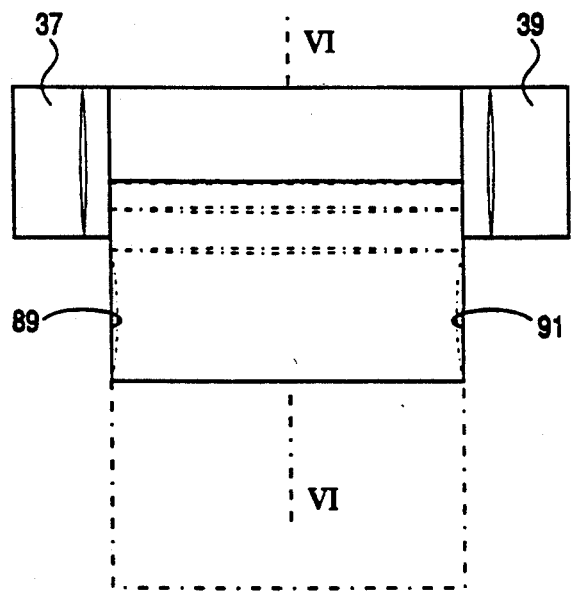
FIG. 5 is a plan view, similar to FIG. 4, showing the fold used to form the envelope region of the accessory drape.
Figure 6:
FIG. 6 is a cross-sectional view taken along lines VI.—VI.
Figure 7:
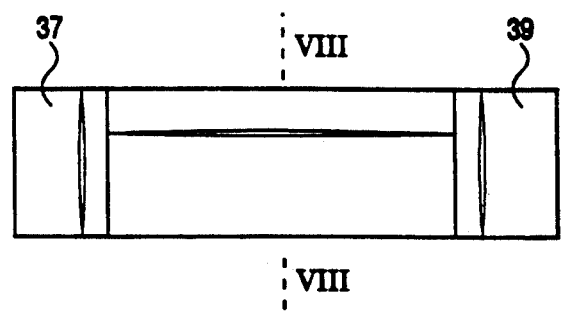
FIG. 7 shows the accessory drape folded in convenient fashion for sterile packaging.
Figure 8:
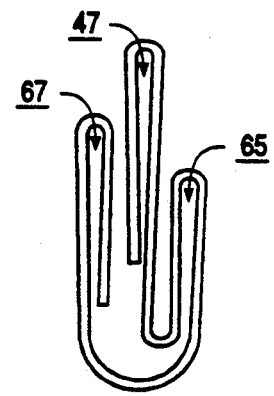
FIG. 8 is a cross-sectional view taken along lines VIII.—VIII.

As best seen in FIG. 3, the drape of the invention is formed from a main sheet of flexible, drapable material 27. A number of flexible materials can conveniently be utilized for this purpose including cloth, thin plastic and even paper. If cloth or paper materials are utilized, they are preferably formed from a water proof material which forms a moisture barrier to prevent fluids present in the accessory pockets (to be described) from penetrating the material of the drape. This can be accomplished in a number of manners, including the provision of a thin plastic layer sandwiched between upper and lower cloth or paper layers, by spraying or coating water pervious materials with a moisture barrier material, or by forming the drape entirely from a water impervious material.

As shown in FIG. 3, the main sheet 27 of flexible, drapable material initially forms a cross-shaped panel of material, the panel having a longitudinal body portion 29 and a cross-arm portion 31 arranged transversely thereto. The longitudinal body portion 29 includes a top panel 33 and a bottom panel 35, the cross-arm portion 31 including outer panels 37, 39 arranged perpendicular to the longitudinal axis 41 of the body portion 29.

Figure 2:
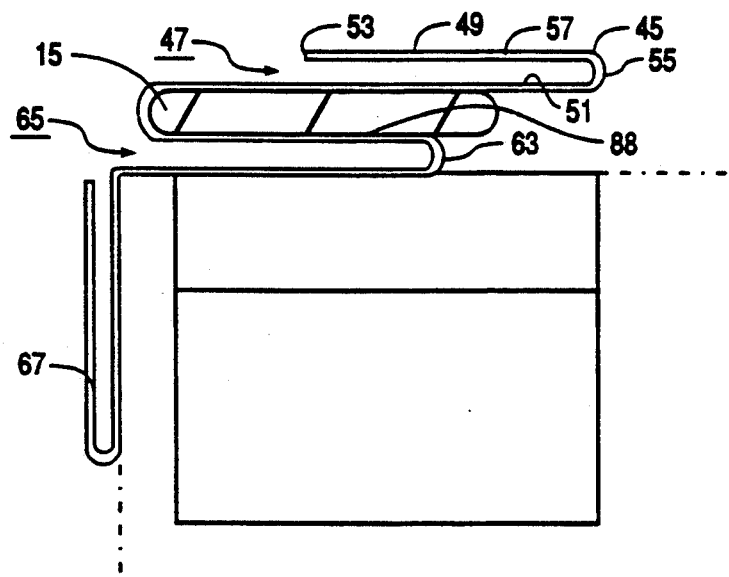
FIG. 2 is a simplified view, taken along lines II.—II.
Figure 9:
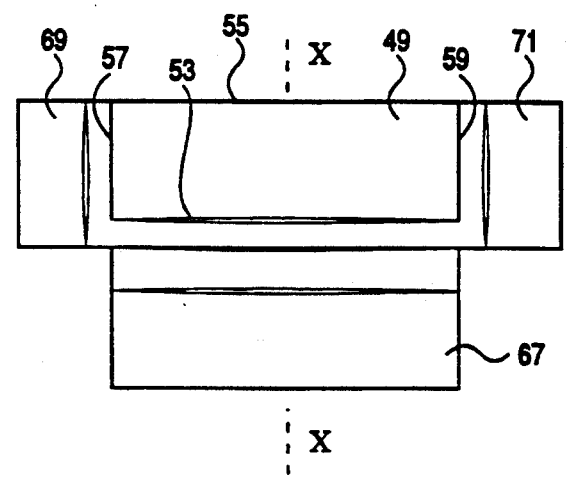
FIG. 9 is a top, plan view of the completed accessory drape of the invention showing the completed folds.

As shown in FIG. 1, the main sheet of flexible, drapable material has a head region 43 which is adapted to be received beneath a patient's head when the patient's head is received on the head support 15 (FIG. 2) for anchoring the drape to the operating table. As best seen in FIG. 2, the head region includes a pocket fold 45 which defines a first accessory receiving pocket 47 for the drape. The first accessory receiving pocket has a top layer 49 a bottom layer 51, each of which has a front edge 53, a rear edge 55 and opposing side edges 57, 59, respectively (see FIG. 9). The front edge 53 of the top layer 49 is recessed to facilitate the insertion of accessories, such as a commercially available suction instrument (61 in FIG. 1).

An envelope region 63 if formed beneath the head region 43 (FIG. 1) of the drapable material. The envelope region defines a second accessory receiving pocket 65 for the drape. The envelope region 63 is adapted to be received beneath the patient head support (cushion 15 in FIG. 2) to thereby further anchor the drape to the patient support structure 13.

As shown in FIGS. 1 and 2, the drape preferably includes at least one additional accessory receiving pocket 67 formed by a pocket fold in the main sheet of flexible, drapable material. The additional accessory receiving pocket 67 is arranged to depend downwardly from the head region 43 of the drape generally perpendicular to the plane thereof when the drape is received on the operating table. If desired, additional accessory receiving pockets 69, 71 can be provided which depend downwardly from the head region 43 of the drape on each of the opposing sides of the table 21, 23, adjacent the head thereof, each of the additional accessory pockets 69, 71 being arranged generally perpendicular to the horizontal plane of rest 25 of the patient.

As shown in FIGS. 3-10, the drape of the invention can be simply and economically formed from the initially cross-shaped piece of material forming the main sheet 27. The head region pocket fold 45 is formed by folding the top panel 33 in the direction of the cross-arm portion 31 (indicated by arrows in FIG. 4), thereby overlaying the cross-arm portion a selected distance. Seams 73, 75 can be provided along either of the opposing side edges, as by heat sealing, sewing or gluing. The outer panels 37, 39 are folded back in the direction of the longitudinal body portion 29 to form additional accessory pockets. The bottom panel 35 of the longitudinal body portion 29 has a lower most extent which is folded back in the direction of the cross-arm portion 31 to form an additional accessory pocket (see FIG. 4). The accessory pockets also have side seams, e.g., 77, 79, 81, 83.

Figure 10:
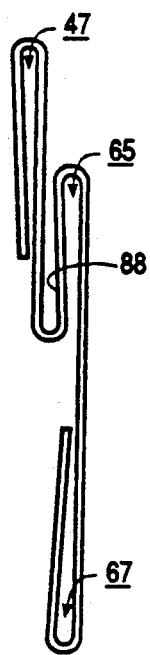
FIG. 10 is a cross-sectional view taken along lines X.—X.

The envelope region 63 can conveniently be formed in the main sheet 27 by folding a first selected length (85 in FIG. 3) back upon a second selected length 87 to create an instrument receiving pocket 65. This pocket can also be provided with side seams 89, 91 (shown by dotted lines in FIG. 5). As shown in FIGS. 2 and 10, the top layer 88 of the envelope region 63 is received beneath the patient head support 15 to further anchor the drape to the operating room table.

Although the invention has been in described in its preferred form, a number of modifications can be envisioned which fall within the scope of the present invention. For instance, for use in a dental office, the accessory drape might be oriented other than at the extreme head of the bed with the envelope region continuing to be received between the cushion and the patient support structure. The accessory drape could also be equipped with other clamps and receptacles to, for instance, crimp off the suction tubing to reduce noise.

An invention has been provided with several advantages. The accessory drape of the invention is simple in design and economical to manufacture. The drape can be provided in disposable form which eliminates the need of laundering and sterilizing drapes for re-use. The drape includes a plurality of accessory receiving pockets receiving instruments such as a suction instrument (61) to reduce contamination of the operating room environment and/or operating room personnel, or subsequent patients, with body fluids which occur in the routine use of suction devices during surgical procedures. The accessory pockets provide a secure means for retaining a variety of surgical instruments while isolating the instruments in sterile fashion. The drape is conveniently received on the head region of a variety of patient support structures such as operating room tables, emergency room tables, stretchers found in emergency rooms, recovery rooms, intensive care units, and the like. The device of the invention reduces contamination of the surrounding area and reduces the chance of exposure of a care-giver, or of a subsequent patient, to a variety of patient contaminants.

While the invention has been shown in only one of its forms, it is not thus limited but is susceptible to various changes and modifications without departing from the spirit thereof.

I claim:

1. A suction drape for use by an anesthesia provider during surgical procedures to temporarily hold a suction instrument, the drape being adapted to be received on a hospital operating room table of the type having a head support for a patient's head at one end thereof, the drape comprising:
   a main sheet of flexible, drapable material, the main sheet having a head region adapted to be received beneath a patient's head when the patient's head is received on the head support for anchoring the drape to the table, the head region including a pocket fold which defines a first accessory receiving pocket for the drape;
   an envelope region formed beneath the head region of the drapable material by folding a portion of the main sheet back upon itself, the envelope region defining a second accessory receiving pocket for the drape, the envelope region being adapted to be received beneath the patient head support of the operating room table to thereby further anchor the drape to the table;
   at least one additional accessory receiving pocket formed by a pocket fold in the main sheet of flexible, drapable material, the additional accessory receiving pocket being arranged to depend downwardly from the head region of the drape generally perpendicular to the plane thereof when the drape is received on the operating room table; and
   wherein the main sheet of flexible, drapable material initially forms a cross-shaped panel of material, the panel having a longitudinal body portion and a cross-arm portion arranged transversely thereto.

2. The suction drape of claim 1, wherein the envelope region is formed in the main sheet by folding a selected length of the body portion back upon itself to thereby create an instrument receiving pocket.

3. The suction drape of claim 2, wherein the longitudinal body portion includes a top panel and a bottom panel, the head region pocket fold being formed by folding the top panel in the direction of the cross-arm portion, thereby overlaying the cross-arm portion a selected distance.

4. The suction drape of claim 3, wherein the cross-arm portion of the main sheet of flexible material includes outer panels which are folded back in the direction of the longitudinal body portion to form additional accessory pockets.

5. The suction drape of claim 4, wherein the bottom panel of the longitudinal body portion has a lowermost extent which is folded back in the direction of the cross-arm portion to form an additional accessory pocket.

6. The suction drape of claim 5, wherein each of the additional accessory pockets, when so formed, has a top layer and a bottom layer, each of which has a front edge, a rear edge and opposing side edges, and wherein the front edge of each of the top layers is recessed to facilitate the insertion of a suction instrument within the pocket.

* * * * *